(12) United States Patent
Ponasik, Jr. et al.

(10) Patent No.: US 6,706,891 B2
(45) Date of Patent: Mar. 16, 2004

(54) PROCESS FOR THE PREPARATION OF LIGANDS FOR OLEFIN POLYMERIZATION CATALYSTS

(75) Inventors: James Allen Ponasik, Jr., Blountville, TN (US); Leslie Shane Moody, Johnson City, TN (US); Peter Borden Mackenzie, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 2 days.

(21) Appl. No.: 09/985,410

(22) Filed: Nov. 2, 2001

(65) Prior Publication Data

US 2003/0013894 A1 Jan. 16, 2003

Related U.S. Application Data

(60) Provisional application No. 60/246,178, filed on Nov. 6, 2000.

(51) Int. Cl.[7] .............................................. C07D 339/02
(52) U.S. Cl. ..................................... 548/523; 549/21
(58) Field of Search ........................... 549/21; 548/523

(56) References Cited

U.S. PATENT DOCUMENTS

| | | |
|---|---|---|
| 4,564,647 A | 1/1986 | Hayashi et al. |
| 4,724,273 A | 2/1988 | Fink et al. |
| 4,752,597 A | 6/1988 | Turner |
| 5,106,804 A | 4/1992 | Bailly et al. |
| 5,132,380 A | 7/1992 | Stevens et al. |
| 5,227,440 A | 7/1993 | Canich et al. |
| 5,296,565 A | 3/1994 | Ueda et al. |
| 5,324,800 A | 6/1994 | Welborn, Jr. et al. |
| 5,331,071 A | 7/1994 | Kataoka et al. |
| 5,332,706 A | 7/1994 | Nowlin et al. |
| 5,350,723 A | 9/1994 | Neithamer et al. |
| 5,399,635 A | 3/1995 | Neithamer et al. |
| 5,466,766 A | 11/1995 | Patsidis et al. |
| 5,468,702 A | 11/1995 | Jejelowo |
| 5,474,962 A | 12/1995 | Takahashi et al. |
| 5,578,537 A | 11/1996 | Hermann et al. |
| 5,863,853 A | 1/1999 | Vaughan et al. |
| 5,866,663 A | 2/1999 | Brookhart et al. |
| 5,880,241 A | 3/1999 | Brookhart et al. |
| 5,880,323 A | 3/1999 | Brookhart, III et al. |
| 5,886,224 A | 3/1999 | Brookhart et al. |
| 5,891,963 A | 4/1999 | Brookhart et al. |
| 6,197,715 B1 | 3/2001 | Bansleben et al. |
| 2002/0049135 A1 * | 4/2002 | Moody et al. ............ 502/123 |

FOREIGN PATENT DOCUMENTS

| | | |
|---|---|---|
| DE | 19707236 A1 | 8/1998 |
| DE | 19944993 A1 | 7/1999 |
| DE | 19959251 A1 | 12/1999 |
| EP | 0 381 495 A2 | 8/1990 |
| EP | 0 416 815 A2 | 3/1991 |
| EP | 0 420 436 A1 | 4/1991 |
| EP | 0 532 098 A1 | 3/1993 |
| EP | 0 641 804 A2 | 3/1995 |
| EP | 0 816 384 A2 | 1/1998 |
| EP | 0 874 005 A1 | 10/1998 |
| EP | 0 884 331 A2 | 12/1998 |
| EP | 0 893 455 A1 | 1/1999 |
| EP | 1 099 714 A1 | 11/1999 |
| JP | 10-324709 | 3/1997 |
| JP | Hei 9-255712 | 9/1997 |
| JP | Hei 9-272709 | 10/1997 |
| JP | Hei 9-272713 | 10/1997 |
| WO | 94/01471 | 1/1994 |
| WO | 94/11410 | 5/1994 |
| WO | 94/14854 | 7/1994 |
| WO | 96/23010 | 8/1996 |
| WO | 97/02298 | 1/1997 |
| WO | 97/17380 | 5/1997 |
| WO | 97/38024 | 10/1997 |
| WO | 97/48735 | 12/1997 |
| WO | 97/48736 | 12/1997 |
| WO | 97/48737 | 12/1997 |
| WO | 97/48739 | 12/1997 |
| WO | 97/48740 | 12/1997 |
| WO | 97/48742 | 12/1997 |
| WO | 97/48777 | 12/1997 |
| WO | 98/03521 A | 1/1998 |
| WO | 98/03559 | 1/1998 |
| WO | 98/11144 | 3/1998 |
| WO | 98/27124 | 6/1998 |
| WO | 98/30609 | 7/1998 |
| WO | 98/30610 | 7/1998 |
| WO | 98/37110 | 8/1998 |
| WO | 98/40374 | 9/1998 |
| WO | 98/40420 | 9/1998 |
| WO | 98/40421 | 9/1998 |
| WO | 98/41529 | 9/1998 |
| WO | 98/42664 | 10/1998 |
| WO | 98/42665 | 10/1998 |
| WO | 98/47933 | 10/1998 |
| WO | 98/47934 | 10/1998 |

(List continued on next page.)

OTHER PUBLICATIONS

A. Bach, et al., "Metal Chelates of N–(1–Pyrrolyl)salicylaldimines and Their Structure Determination by X–Ray Structure Analysis and X–Ray Absorption Spectroscopy (XANES)," Z. Naturforsch., Chem. Sci., 1996, pp. 757–764, vol. 51 (6).

A. V. Bordunov, et al., "Azacrown Ethers Containing Oximic and Schiff Base Sidearms—Potential Heteronuclear Metal Ion Receptors," Tetrahedron, NL, Dec. 29, 1997, pp. 17595–17606, vol. 53, No. 52, Elsevier Science Publishers, Amsterdam.

(List continued on next page.)

Primary Examiner—Joseph K. McKane
Assistant Examiner—Andrea D. Small
(74) Attorney, Agent, or Firm—Jonathan D. Wood; Bernard J. Graves, Jr.

(57) ABSTRACT

Processes for the preparation of 4,5-bisimino-[1,3]dithiolanes and 2,3-bisimino-[1,4]dithianes are described. The processes involve conversion of an oxalamide to a dithiooxalamide, followed by conversion of the dithiooxalamide to either a 4,5-bisimino-[1,3]dithiolane or a 2,3-bisimino-[1,4]dithiane.

16 Claims, No Drawings

FOREIGN PATENT DOCUMENTS

| WO | 98/56832 | 12/1998 |
| --- | --- | --- |
| WO | 99/02472 | 1/1999 |
| WO | 99/02570 | 1/1999 |
| WO | 00/47592 A1 | 2/1999 |
| WO | 99/05189 | 2/1999 |
| WO | 99/09078 | 2/1999 |
| WO | 00/58320 A1 | 3/1999 |
| WO | 99/10391 | 3/1999 |
| WO | 99/12981 | 3/1999 |
| WO | 01/07491 A1 | 7/1999 |
| WO | 01/12684 A1 | 8/1999 |
| WO | 01/07492 A1 | 9/1999 |
| WO | 01/14391 A1 | 9/1999 |
| WO | 01/21586 A1 | 9/1999 |
| WO | 01/23396 A1 | 9/1999 |
| WO | 01/42257 A1 | 12/1999 |
| WO | 99/62968 A | 12/1999 |
| WO | 00/04057 | 1/2000 |
| WO | 01/55231 A1 | 1/2000 |
| WO | 00/50470 A | 8/2000 |
| WO | 01/92342 A | 12/2001 |

OTHER PUBLICATIONS

M. Brookhart et al., *J. Am. Chem. Soc.*, 1995, pp. 6414–6415, 117.

Buelow, "Chemische Berichte," *Berichte Der Deutschen Chemischen Gesellschaft, DE, Verlag Chemie, Weinheim*, 1905, pp. 3915, 3917, vol. 38.

R. M. Claramunt, et al., "Rhodium (I) Complexes with the Polydentate Ligand 3,5–bis(4–methylpyrazol–1–yl)–4–methylpyrazole,"*Journal Organometallic Chemistry*, 1991, pp. 259–271, vol. 412, No. 1–2.

I. O. Fritsky, et al., "Template Synthesis of Square–Planar Nickel (II) and Copper (III) Complexes Based on Hydrazide Ligands," *J. Chem. Soc., Dalton Trans.*, 1998, pp. 3269–3274, vol. 19.

V. C. Gibson et al., *Chem. Commun.*, 1998, pp. 313–314.

S. D. Ittel et al., "Late–Metal Catalysts for Ethylene Homo– and Copolymerization," *Chem. Rev.*, 2000, pp. 1169–1203, 100.

W. Keim et al., *Angew Chem. Int. Ed. Engl.*, 1981, pp. 116–117, 20.

D. H. McConville et al., *J. Am. Chem. Soc.*, 1996, pp. 10008–10009, 118.

V. M. Mohring et al.,*Agnew. Chem. Int. Ed. Engl.*, 1985, pp. 1001–1003, 24.

K. K. Narang, et al., Glyoxal–Aroyl Hydrazone (Schiff Base) Complexes of Nickel (II), Copper (III) & Zinc (III), *Indian J. Chem., Sect. A.*, pp. 830–832, vol. 21A(8).

K. K. Narang, et al., "Synthesis, Characterization, Thermal Studies and Biological Activity of Iron (III) Complexes with Some Acylhydrazines," *Synth. React. Inorg. Met.–Org. Chem.*, 1993, pp. 971–989, vol. 23(6).

F. A. Neugebauer, "ESR Studies of 1,2,4,5–Tetraazapentenyls," *Chem. Ber.,*, 1973, pp. 1716–1723, vol. 106(6).

M. Peuckert et al., *Organometallics*, 1983, pp. 594–597, 2.

S. B. Roscoe et al., "Polyolefin Spheres from Metallocenes Supported on Noninteracting Polystyrene," *Science*, 1998, pp. 270–273, 280.

L. Rosenberg, et al., "Binuclear Nickel (III) and Cobalt (II) Complexes of the Novel Binucleating Ligand 3,–Bis(1'–pyrazolyl)pyridazine, Crystal and Molecular Structure and Magnetism of Bis[$\mu$–3,6–bis(1'pyrazolyl–pyridazine–$N^1(Ni^1)N^2(Ni^1)N^2(Ni^1)N^2(Ni^2)N^2(Ni^{2'})$]–bis[diaquanickel (III) ]Tetrachloride Dihydrate," *J. Chem. Soc., Dalton Trans.*, 1986, pp. 625–631, vol. 3.

M. Schmid et al., "New $C_{2V}$ and Chiral $C_2$–Symmetric Olefin Polymerization Catalysts Based on Nickel (III) and Palladium (II) Diimine Complexes Bearing 2,6–Diphenyl Aniline Moieties: Synthesis, Structural Characterization, and First Insight into Polymerization Properties," *Organometallics*, 2001, 20(11), 2321.

R. R. Schrock et al., *J. Am. Chem. Soc.*, 1997, pp. 3830–3831, 119.

R. R. Schrock et al., *J. Am. Chem. Soc.*, 1999, pp. 5797–5798, 121.

S. H. Strauss, *Chem. Rev.*, 1993, pp. 927–942, 93.

A. A. Watson, et al., "Chiral Heterocyclic Ligands. VIII. Syntheses and Complexes of New Chelating Ligands Derived from Camphor," *Aust. J. Chem.*, 1995, pp. 1549–1572, vol. 48, No. 9.

Louis A. Carpino, "Alkaline Degradation of 1,1–disubstituted 2–arenesulfonhydrazides. Synthesis and Reactivity of 1–Amino–2,5–diphenyl– and –2,3,4,5–tetraphenylpyrrole," *J. Org. Chem.*, 1965, pp. 736–739, vol. 30.

Dieter Enders and Michaela Meiers, "Diastereo– and Enantioselective Synthesis of $C_2$–Symmetric, Protected 1,n–Diamines from Dialdehydes," *Angew. Chem. Int. Ed. Engl.*, 1996, pp. 2261–2263, vol. 35, No. 19.

Time Repo, et al., "Ethylenebis(Salicylidenetiminato)zirconium Dichloride: Crystal Structure and Use as a Heterogeneous Catalyst in the Polymerization of Ethylene," *Maromolecules*, (1997), 171–175, 30.

Oleg V. Mikhailov, "From Novel Complexing Conditions to Novel Coordination Compounds of Nickel (III) with Dithiooxamide and its Bulky Analogues," *Transition Met. Chem.*, (1996), 363–369, 21.

\* cited by examiner

PROCESS FOR THE PREPARATION OF LIGANDS FOR OLEFIN POLYMERIZATION CATALYSTS

CROSS REFERENCE TO RELATED APPLICATION

This is a non-provisional application of U.S. Provisional Application No. 60/246,178, filed Nov. 6, 2000; the entire contents of which are hereby incorporated by reference.

FIELD OF THE INVENTION

The invention relates to processes for the preparation of 4,5-bisimino-[1,3]dithiolanes and 2,3-bisimino-[1,4] dithianes. Certain of these processes have two-step sequences involving (i) conversion of an oxalamide to a dithiooxalamide, followed by (ii) conversion of the dithiooxalamide to either a 4,5-bisimino-[1,3]dithiolane or a 2,3-bisimino-[1,4]dithiane. 4,5-bisimino-[1,3]dithiolanes and 2,3-bisimino-[1,4]dithianes are useful as ligands for olefin polymerization catalysts (U.S. Pat. No. 6,103,658; PCT Intl. Appl. WO 0050470A2).

BACKGROUND OF THE INVENTION

Nickel and palladium complexes of bidentate N,N-donor ligands have recently been shown to be useful as olefin polymerization catalysts (Ittel et al., *Chem. Reviews* 2000, 100, 1169). There is a need therefore for efficient methods of synthesizing such ligands. In addition to the methods described in the literature reviewed by Ittel et al. (*Chem. Reviews* 2000, 100, 1169), Gonioukh et al. (WO 01/21586 A1) have recently described methods for this purpose. Notwithstanding these developments, there remains a need for further improvements in efficiency and scope to provide general and cost effective routes to such ligands.

SUMMARY OF THE INVENTION

In a first aspect, this invention provides a straightforward, efficient and cost effective process for the preparation of a 4,5-bisimino-[1,3]dithiolane or a 2,3-bisimino-[1,4]dithiane of general formula I, useful as ligands for olefin polymerization catalysts;

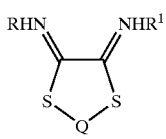

wherein an oxalamide of general formula II

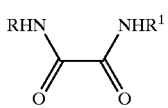

is reacted with a reagent capable of transforming an amide to a thioamide, which is then reacted with a reagent of general formula III;

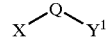

wherein,
R and $R^1$ are each, independently hydrocarbyl, substituted hydrocarbyl, heteroatom connected hydrocarbyl or heteroatom connected substituted hydrocarbyl;
Q is hydrocarbyl or substituted hydrocarbyl; and
X and $Y^1$ are each, independently, a leaving group.

In a second aspect, this invention relates to a straightforward, efficient and cost effective process for the preparation of compounds of the general formula IV, useful as ligands for olefin polymerization catalysts, in a single reactor, without isolation of any intermediates;

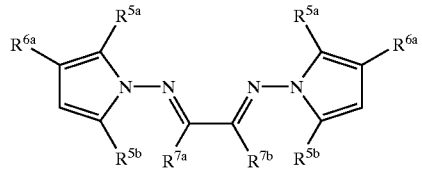

wherein a diketone of general formula V is reacted with a protected hydrazine in the presence of an acid to form a protected amino pyrrole, the resultant protected amino pyrrole is then reacted with an α-diketone of general formula VI in the presence of an acid;

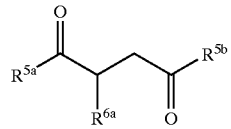

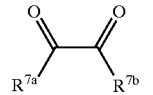

wherein:
$R^{5a}$ and $R^{5b}$ are each, independently, hydrocarbyl, substituted hydrocarbyl, heteroatom connected hydrocarbyl or heteroatom connected substituted hydrocarbyl;
$R^{6a}$ is H, hydrocarbyl, substituted hydrocarbyl, heteroatom connected hydrocarbyl or heteroatom connected substituted hydrocarbyl; and
$R^{7a}$ and $R^{7b}$ are each hydrocarbyl, substituted hydrocarbyl, heteroatom connected hydrocarbyl, or heteroatom connected substituted hydrocarbyl.

DETAILED DESCRIPTION OF THE INVENTION

In a first aspect, this invention relates to a process for the preparation of a 4,5-bisimino-[1,3]dithiolane or a 2,3-bisimino-[1,4]dithiane of general formula I by reacting a substituted oxalamide of general formula II with a reagent capable of transforming an amide to a thioamide to form a dithiooxalamide compound. The second step of the process involves reaction of the dithiooxalamide compound with a compound of general formula III to provide the 4,5-bisimino-[1,3]dithiolane or 2,3-bisimino-[1,4]dithiane of general formula I. This process, along with preferred embodiments, is described in more detail in the discussion and examples below.

The oxalamide may be any oxalamide of general formula II, which may be prepared by any number of methods known to those skilled in the art, including, but not limited to, reaction of oxalic dihydrazide with a 1,4-diketone and reaction of a primary amine with oxalyl chloride. Preferred R and $R^1$ groups in general formula II are chosen from the group consisting of

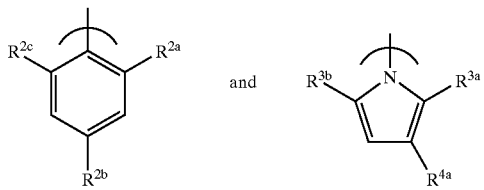

wherein:
$R^{2a-2c}$ are each, independently, H, hydrocarbyl, substituted hydrocarbyl, heteroatom connected hydrocarbyl or heteroatom connected substituted hydrocarbyl; $R^{3a-3b}$ are each, independently hydrocarbyl, substituted hydrocarbyl, heteroatom connected hydrocarbyl or heteroatom connected substituted hydrocarbyl; and $R^{4a}$ is H, hydrocarbyl, substituted hydrocarbyl, heteroatom connected hydrocarbyl or heteroatom connected substituted hydrocarbyl. Preferably $R^{2a}$ and $R^{2c}$ are each, independently, hydrocarbyl, substituted hydrocarbyl, heteroatom connected hydrocarbyl or heteroatom connected substituted hydrocarbyl. More preferably, $R^{2a}$ and $R^{2c}$ are each, independently, hydrocarbyl or substituted hydrocarbyl. Examples of suitable $R^{2a}$ and $R^{2c}$ groups include, but are not limited to, methyl, ethyl, isopropyl, isobutyl, tert-butyl, phenyl, 4-tert-butyl phenyl, 4-methyl phenyl, 4-methoxy phenyl, 4-trifluoromethyl phenyl, 4-nitro phenyl and 3,5-diphenyl phenyl.

Preferably, $R^{3a}$ and $R^{3b}$ are each, independently, hydrocarbyl or substituted hydrocarbyl. Examples of suitable $R^{3a}$ and $R^{3b}$ groups include, but are not limited to, methyl, ethyl, isopropyl, isobutyl, tert-butyl, phenyl, 4-tert-butyl phenyl, 4-methyl phenyl, 4-methoxy phenyl, 4-nitro phenyl and 3,5-diphenyl phenyl.

Preferably, $R^{4a}$ is H, hydrocarbyl or substituted hydrocarbyl. Examples of suitable $R^{4a}$ groups include, but are not limited to, H, methyl, ethyl, isopropyl, tert-butyl, isobutyl, phenyl, —COOR$^5$, —COR, —CONR$^5{}_2$, —CONHR$^5$, cyano and nitro; wherein $R^5$ is hydrocarbyl or substituted hydrocarbyl. Examples of suitable $R^5$ groups include, but are not limited to, methyl, ethyl, isopropyl, tert-butyl, isobutyl and phenyl.

Examples of a reagent capable of transforming an amide to a thioamide include, but are not limited to, $P_4S_{10}$ and 2,4-bis(4-methoxyphenyl)-1,3-dithia-2,4-diphosphetane-2,4-disulfide.

The first step of the process may be run in an inert solvent, preferably toluene or xylene. When phosphorous pentasulfide is used as the source of sulfur, the reaction may be conducted at temperatures ranging from about 25 to about 200° C., preferably at temperatures ranging from about 75 to about 150° C. With other sources of sulfur, the preferred temperature range will generally be similar but will best be determined by routine experimentation. Pressures at or above about 1 atm are preferred.

Step two of the process to prepare a 4,5-bisimino-[1,3] dithiolane or a 2,3-bisimino-[1,4]dithiane of general formula I involves reaction of the dithiooxalamide formed in step (i) of the process with a compound of general formula III; wherein Q is hydrocarbyl or substituted hydrocarbyl; and X and $Y^1$ are each, independently, leaving groups. Preferably, Q is —CH$_2$CH$_2$—, —CH$_2$—, —CO— or —CS—; more preferably, Q is —CH$_2$CH$_2$—. When X and $Y^1$ are both bromo and Q is —CH$_2$CH$_2$—, the reaction may be conducted at temperatures ranging from about 0 to about 100° C., preferably at temperatures ranging from about 25 to about 50° C. With other X, $Y^1$, and Q, the preferred temperature range will generally be similar but will best be determined by routine experimentation. Pressures at or above about 1 atm are preferred.

A "leaving group" is any species that can be expelled by a nucleophile in an $S_N2$ reaction or is easily dissociated in an $S_N1$ reaction. Examples of suitable leaving groups include, but are not limited to, chloride, bromide, p-toluene sulfonate, methane sulfonate and trifluoromethane sulfonate. Preferably, X and $Y^1$ are each, independently, bromide.

Step (ii) of the process may further comprise a base to aid in the removal of the acidic dithiooxalamide proton. Preferably, the base is an alkali metal hydroxide or ammonium hydroxide. Preferred alkali metal hydroxides are sodium hydroxide and potassium hydroxide.

Step (ii) of the process may be run in neat compound III, as a solution in an inert organic solvent, in a biphasic mixture of compound III and water, or as a biphasic mixture of an inert organic solvent and water. When the reaction is run as a biphasic mixture, a phase transfer catalyst may also be present. A non-limiting example of a phase transfer catalyst is tetrabutyl ammonium bromide.

In a second aspect, this invention relates to a process for the preparation of a compound of general formula IV in three steps, which may be carried out in a single reaction vessel without isolation of the intermediate products.

The first step of the process of the second aspect involves the condensation of a protected hydrazine with a diketone of general formula V in the presence of an acid and an alcohol solvent to provide a protected 2,5-disubstituted, optionally 3-substituted, 1-amino pyrrole. Examples of suitable protected hydrazines include, but are not limited to, tert-butyl carbazate and hydrazine carboxylic acid 2-trimethylsilanyl-ethyl ester. Examples of suitable diketones of general formula V include, but are not limited to, dibenzoyl ethane and 2-benzoyl-4-oxo-4-phenyl-butyric acid ethyl ester. Examples of suitable acids include, but are not limited to, acetic acid and para-toluene sulfonic acid. Examples of suitable alcohol solvents include, but are not limited to, methanol, ethanol and isopropanol. The reaction may be conducted at temperatures ranging from about 25 to about 150° C., preferably at temperatures ranging from about 50 to about 115° C. Pressures at or above about 1 atm are preferred.

The second step of the process of the second aspect involves deprotection of the 1-amino pyrrole prepared in the first step in the presence of an acid in an alcohol solvent. Examples of suitable acids include hydrochloric acid, trifluoroacteic acid, phosphoric acid and sulfuric acid. Examples of suitable alcohol solvents include methanol, ethanol and isopropanol. The reaction may be conducted at temperatures ranging from about 0 to about 200° C., preferably at temperatures ranging from about 25 to about 115° C. Pressures at or above about 1 atm are preferred.

The third step of the process of the second aspect involves the condensation of the 1-amino pyrrole prepared in the second step, with an α-diketone of general formula VI in the presence of an acid and alcohol solvent. Examples of suitable α-diketones include, but are not limited to, 2,3-butanedione, benzil and 3,4-hexanedione. Examples of suitable acids include, but are not limited to, hydrochloric acid, sulfuric acid and phosphoric acid. Examples of suitable alcohol solvents include, but are not limited to, methanol, ethanol and isopropanol. The reaction may be conducted at temperatures ranging from about 0 to about 150° C., preferably at temperatures ranging from about 25 to about 115° C. Pressures at or above about 1 atm are preferred.

$R^{5a}$ and $R^{5b}$ are each, independently, hydrocarbyl or substituted hydrocarbyl, more preferably phenyl, 4-trifluoromethylphenyl, 4-tert-butylpehnyl or 4-methylphenyl.

$R^{6a}$ is H, hydrocarbyl, substituted hydrocarbyl, heteroatom connected hydrocarbyl or heteroatom connected substituted hydrocarbyl. Preferably, $R^{6a}$ is H, methyl, hydroxymethyl, cyano, nitro or —$COOR^{8a}$, wherein $R^{8a}$ is hydrocarbyl or substituted hydrocarbyl, preferably methyl or ethyl.

$R^{7a}$ and $R^{7b}$ are each hydrocarbyl or substituted hydrocarbyl. Preferably, $R^{7a}$ and $R^{7b}$ are each, independently, methyl, ethyl, phenyl, aryl, or isopropyl. Additionally, $R^{7a}$ and $R^{7b}$ may be linked to form a bridging group. Preferred bridging groups include, but are not limited to 1,2-phenylene and 1,8-naphthylene.

A "hydrocarbyl" group means a monovalent or divalent, linear, branched or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from $C_1$–$C_{20}$ alkyl, $C_3$–$C_8$ cycloalkyl, and aryl; $C_3$–$C_8$ cycloalkyl; $C_3$–$C_8$ cycloalkyl substituted with one or more groups selected from $C_1$–$C_{20}$ alkyl, $C_3$–$C_8$ cycloalkyl, and aryl; $C_6$–$C_{14}$ aryl; and $C_6$–$C_{14}$ aryl substituted with one or more groups selected from $C_1$–$C_{20}$ alkyl, $C_3$–$C_8$ cycloalkyl, and aryl; where the term "aryl" preferably denotes a phenyl, napthyl, or anthracenyl group. Examples of divalent (bridging) hydrocarbyls include: —$CH_2$—, —$CH_2CH_2$—, —$CH_2CH_2CH_2$—, naphthalene-1,8-diyl, and 1,2-phenylene.

A "substituted hydrocarbyl" refers to a monovalent or divalent hydrocarbyl substituted with one or more heteroatoms. Examples of monovalent substituted hydrocarbyls include: 2,6-dimethyl-4-methoxyphenyl, 2,6-diisopropyl-4-methoxyphenyl, 4-cyano-2,6-dimethylphenyl, 2,6-dimethyl-4-nitrophenyl, 2,6-difluorophenyl, 2,6-dibromophenyl, 2,6-dichlorophenyl, 4-methoxycarbonyl-2,6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl-4-trimethylammoniumphenyl (associated with a weakly coordinated anion), 2,6-dimethyl-4-hydroxyphenyl, 9-hydroxyanthr-10-yl, 2-chloronapth-1-yl, 4-methoxyphenyl, 4-nitrophenyl, 9-nitroanthr-10-yl, —$CH_2OCH_3$, cyano, trifluoromethyl, and fluoroalkyl. Examples of divalent (bridging) substituted hydrocarbyls include: 4-methoxy- 1,2-phenylene, 1-methoxymethyl-1,2-ethanediyl, 1,2-bis(benzyloxymethyl)-1,2-ethanediyl, and 1-(4-methoxyphenyl)-1,2-ethanediyl.

A "heteroatom connected hydrocarbyl" refers to a group of the type $E^1$(hydrocarbyl), $E^2$H(hydrocarbyl), or $E^2$(hydrocarbyl)$_2$, where $E^1$ is an atom selected from Group 16 and $E^2$ is an atom selected from Group 15.

A "heteroatom connected substituted hydrocarbyl" refers to a group of the type $E^1$(substituted hydrocarbyl), $E^2$H(substituted hydrocarbyl), or $E^2$(substituted hydrocarbyl)$_2$, where $E^1$ is an atom selected from Group 16 and $E^2$ is an atom selected from Group 15.

A "bridging group" refers to an atom or group which links two or more groups, which has an appropriate valency to satisfy its requirements as a bridging group. Suitable examples include divalent or trivalent hydrocarbyl, substituted hydrocarbyl, heteroatom connected hydrocarbyl, heteroatom connected substituted hydrocarbyl, substituted silicon(IV), boron(III), N(III), P(III), and P(V), —C(O)—, —$SO_2$—, —C(S)—, —B(OMe)—, —C(O)C(O)—, O, S, and Se. In some cases, the groups which are said to be "linked by a bridging group" are directly bonded to one another, in which case the term "bridging group" is meant to refer to that bond.

A further understanding can be obtained by reference to certain specific examples which are provided herein for purpose of illustration only and are not intended to be limiting.

EXAMPLES

Example 1

Synthesis of aaa13

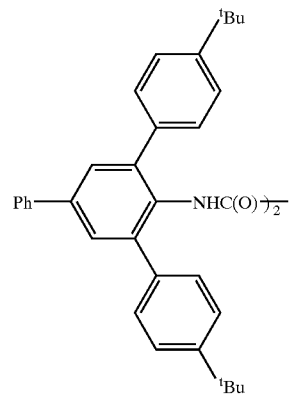

2,6-bis(4-t-butylphenyl)-4-phenyl aniline (5.1 g, 11.76 mmol) was dissolved in pyridine (5 mL) and treated with 4-(dimethylamino)-pyridine (30 mg). Under an atmosphere of dry nitrogen gas, oxalyl chloride (515 mL, 5.88 mmol) was added dropwise. The mixture was stirred ca. 72 h at 23° C., then heated to 60° C. for 2 h more. After cooling to 23° C., TLC analysis indicated that some of the aniline remained unreacted, but the desired product was the major component of the reaction mixture. The reaction mixture was treated with methanol to precipitate the desired product. The white powder was collected by vacuum filtration, and washed with methanol to afford 4.4 g aaa13.

Example 2

Synthesis of aaa14

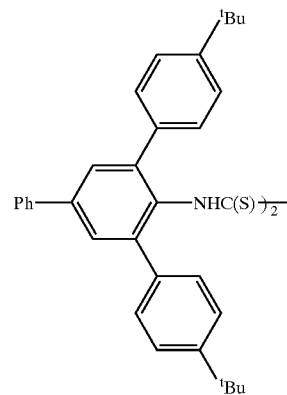

A suspension of aaa13 (4.4 g, 4.78 mmol) in ortho-xylene (20 ml) was treated with phosphorus pentasulfide (1.1 g, 2.39 mmol). The flask was fitted with a reflux condenser, and immersed in a 180° C. oil bath. The resulting suspension was refluxed under nitrogen for ca. 3 h, then cooled to 23° C.,

Example 3
Synthesis of aaa15 then diluted with ca. 35 mL methylene chloride. The heterogeneous mixture was poured onto a column of silica (10"×50 mm) and eluted with methylene chloride/hexane, collecting only the forerunning orange band. Upon concentration, aaa14 crystallized from solution as orange needles (2 g), and was collected by filtration. The filtrate was concentrated to give more aaa14 as an orange crystalline powder (1.8 g).

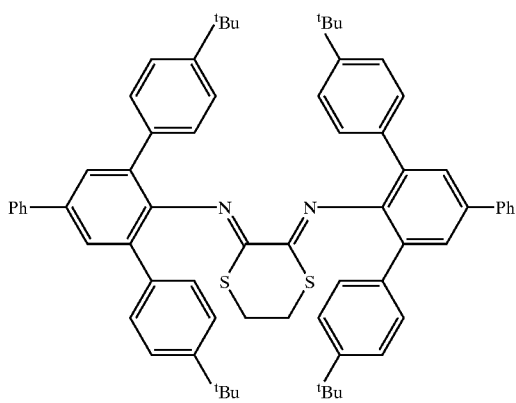

aaa15

A suspension of aaa14 (2 g, 2.1 mmol) in 1,2-dibromoethane (7 ml) was treated with tetrabutylammonium bromide (15 mg) and 2 N aq NaOH (10 mL). The biphasic mixture was stirred vigorously for 1.5 h. The color discharged markedly and a pale precipitate separated. The mixture was diluted with methylene chloride (200 mL) and water (200 mL). The layers were separated, and the organic layer was washed with water (2×50 mL). The organic layer was concentrated to 50 mL, the treated with methanol. aaa15 crystallized as short pale yellow needles (1.19 g, $1^{st}$ crop). A second crop eventually crystallized from the filtrate (0.66 g). A third crop was obtained by treating the filtrate of the second with a few mLs of water (110 mg).

Example 4
Synthesis of aaa10

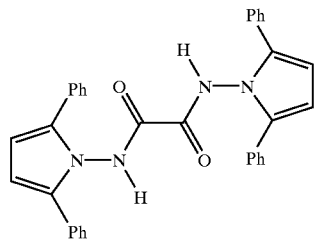

aaa10

A suspension of dibenzoyl ethane (8.8 g, 37 mmol) in toluene (15 ml) and 1-methyl-2-pyrrolidinone (7.5 ml) was treated with oxalic dihydrazide (2 g, 17 mmol). The flask was fitted with a Dean Stark trap, and immersed in a 170° C. oil bath. The resulting suspension was stirred under Ar, with azeotropic removal of water until all of the starting diketone was consumed (determined by TLC), then cooled to 23° C. The solvent was removed in vacuo. The dark oily residue was washed with MeOH and filtered to afford a mixture (4.21 g) of N,N'-bis(2,5-diphenyl-1-pyrrolyl) oxamide contaminated with an unidentified impurity (on the order of 50–65% by weight), which was used without purification.

Example 5
Synthesis of aaa11

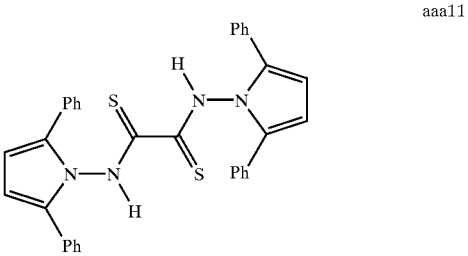

aaa11

A suspension of impure aaa10 from Example 4 (523 mg) in ortho-xylene (6 ml) was treated with phosphorus pentasulfide (222 mg, 0.5 mmol). The flask was fitted with a reflux condenser, and immersed in a 180° C. oil bath. The resulting suspension was refluxed under nitrogen for ca. 2 h, then cooled to 23° C., then diluted with ca. 35 mL methylene chloride. The heterogeneous mixture was poured onto a column of silica (10"×50 mm) and eluted with methylene chloride/toluene (3/2), collecting only the forerunning orange-red band. The solvent was removed in vacuo to give aaa11 as deep violet needles (yield 121 mg).

Example 6
Synthesis of aaa12

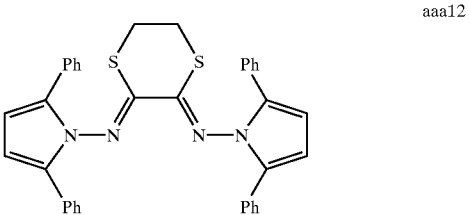

aaa12

A suspension of aaa11 (566 mg, 1.02 mmol) in 1,2-dibromoethane (7 ml) was treated with tetrabutylammonium bromide (15 mg) and 2 N aq NaOH (10 mL). The biphasic mixture was stirred vigorously for 15 min. The color discharged markedly and a pale precipitate separated almost immediately on stirring. The mixture was diluted with methylene chloride (200 mL) and water (200 mL). The layers were separated, and the organic layer was washed with water (2×50 mL) and dried (MgSO$_4$), concentrated, and adsorbed onto silica, then chromatographed over silica eluting with methylene chloride/hexane. The solvent was removed in vacuo to give aaa12 as an orange-yellow powder (yield 520 mg).

Example 7

Synthesis of aaa1

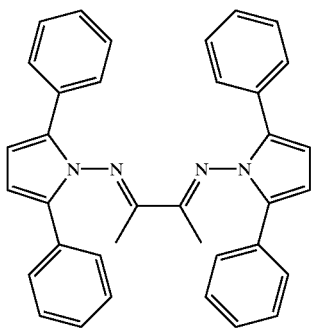

aaa1

A mixture of dibenzoyl ethane (5 g, 21.0 mmol) and tert-butyl carbazate (3.05 g, 23.1 mmol) was treated with ethanol (62.5 ml) and glacial acetic acid (7.6 ml). The resulting suspension was immersed in a 100° C. oil bath, and stirred under Ar for 17.5 h, then cooled to room temperature. The solution was treated with 2,3-butane dione (920 μl, 10.5 mmol) and sulfuric acid (4.2 ml). The resulting dark solution was immersed in an 80° C. oil bath, and stirred under Ar for 30 min, then cooled to room temperature. As the solution cooled, copious orange/yellow solid crystallized. The crystals were filtered washed with cold ethanol, and dried in vacuo to afford aaa1 (4.3 g, 79%).

We claim:

1. A process for preparing a compound of general formula I comprising the steps of:

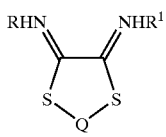

I (i) reacting an oxalamide of general formula II with a reagent capable of transforming an amide to a thioamide to form a dithiooxalamide compound; and

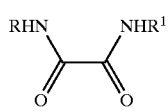

II (ii) reacting the dithiooxalamide compound of step (i) with a compound of formula III;

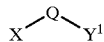

III wherein,

R and $R^1$ are each, independently hydrocarbyl, substituted hydrocarbyl, heteroatom connected hydrocarbyl or heteroatom connected substituted hydrocarbyl;

Q is hydrocarbyl or substituted hydrocarbyl; and

X and $Y^1$ are each, independently, a leaving group.

2. The process according to claim 1, wherein the reagent capable of transforming an amide to a thioamide is $P_4S_{10}$ or 2,4-bis(4-methoxyphenyl)-1,3-dithia-2,4-diphosphetane-2,4-disulfide.

3. The process according to claim 1, wherein step (ii) is conducted in the presence of an alkali metal hydroxide or ammonium hydroxide.

4. The process according to claim 1, wherein step (ii) is conducted in the presence of a phase transfer catalyst.

5. The process according to claim 1, wherein X and $Y^1$ are selected from the group consisting of chloride, bromide, p-toluene sulfonate, methane sulfonate and trifluoromethane sulfonate.

6. The process according to claim 5, wherein X and $Y^1$ are both Br.

7. The process according to claim 1, wherein Q is selected from the group consisting of —$CH_2CH_2$—, —$CH_2$—, —CO— and —CS—.

8. The process according to claim 7, wherein Q is —$CH_2CH_2$—.

9. The process according to claim 1, wherein R and $R^1$ are each, independently, chosen from the group consisting of

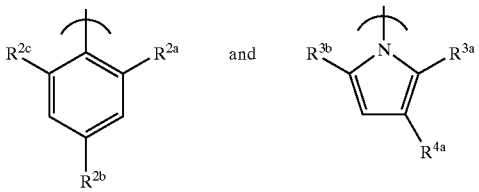

wherein $R^{2a-c}$ are each, independently, H, hydrocarbyl, substituted hydrocarbyl, heteroatom connected hydrocarbyl or heteroatom connected substituted hydrocarbyl;

$R^{3a,b}$ are each, independently hydrocarbyl, substituted hydrocarbyl, heteroatom connected hydrocarbyl or heteroatom connected substituted hydrocarbyl; and $R^{4a}$ is H, hydrocarbyl, substituted hydrocarbyl, heteroatom connected hydrocarbyl or heteroatom connected substituted hydrocarbyl.

10. The process according to claim 9, wherein the reagent capable of transforming an amide to a thioamide is $P_4S_{10}$ or 2,4-bis(4-methoxyphenyl)-1,3-dithia-2,4-diphosphetane-2,4-disulfide.

11. The process according to claim 9, wherein step (ii) is carried out in the presence of an alkali metal hydroxide or ammonium hydroxide.

12. The process according to claim 9, wherein step (ii) is carried out in the presence of a phase transfer catalyst.

13. The process according to claim 9, wherein X and $Y^1$ are selected from the group consisting of chloride, bromide, p-toluene sulfonate, methane sulfonate and trifluoromethane sulfonate.

14. The process according to claim 13, wherein X and $Y^1$ are Br.

15. The process according to claim 9, wherein Q is selected from the group consisting of —$CH_2CH_2$—, —$CH_2$—, —CO— and —CS—.

16. The process according to claim 15, wherein Q is —$CH_2CH_2$—.

* * * * *